US012636057B2

(12) United States Patent     (10) Patent No.:   US 12,636,057 B2

Oglaza et al.                         (45) Date of Patent:     May 26, 2026

(54) DEVICE INCLUDING AN EXPANDABLE IMPLANT AND ANCHORING ELEMENTS FOR ANCHORING THE DEVICE WITHIN A VERTEBRAL PEDICLE

(71) Applicant: Stryker Corporation, Kalamazoo, MI (US)

(72) Inventors: Jean-Francois Oglaza, Pins-Justaret (FR); Gabriel James Harshman, Portage, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/721,721

(22) PCT Filed: Dec. 19, 2022

(86) PCT No.: PCT/US2022/053335

§ 371 (c)(1),
(2) Date: Jun. 19, 2024

(87) PCT Pub. No.: WO2023/122005

PCT Pub. Date: Jun. 29, 2023

(65) Prior Publication Data

US 2025/0057574 A1     Feb. 20, 2025

Related U.S. Application Data

(60) Provisional application No. 63/291,712, filed on Dec. 20, 2021.

(51) Int. Cl.
    A61B 17/88       (2006.01)
    A61B 17/84       (2006.01)
(52) U.S. Cl.
    CPC .......... A61B 17/8858 (2013.01); A61B 17/84 (2013.01)

(58) Field of Classification Search
    CPC ............ A61B 17/7258; A61B 17/8858; A61B 17/7065; A61B 17/7266; A61B 17/7275
          (Continued)

(56) References Cited

U.S. PATENT DOCUMENTS 6,780,185 B2    8/2004   Frei et al.
7,846,206 B2   12/2010   Oglaza et al.
          (Continued)

FOREIGN PATENT DOCUMENTS

EP       1749490 A1 *   2/2007   .......... A61B 17/863
EP       2074956 A1     7/2009
          (Continued)

OTHER PUBLICATIONS

International Search Report for Application No. PCT/US2022/053335 dated Apr. 25, 2023, 3 pages.

*Primary Examiner* — Eduardo C Robert
(74) *Attorney, Agent, or Firm* — Howard & Howard Attorneys PLLC

(57)             ABSTRACT

A device for augmenting a vertebra. The device includes an expandable implant and a pedicle anchor. The pedicle anchor includes at least one anchoring element movably coupled to an anchor body. An actuator is movable within the anchor body to deploy the anchoring element into engagement with a vertebral pedicle. The anchoring element may be deployed in a same plane as a tissue support ski of the expandable implant. The actuator may be a rod including a knuckle or a cam. The tissue support ski may be recessed from an outer profile of the device. Struts of the expandable implant may be angled towards the tissue support ski in an insertion configuration. The device may be oval-shaped and provide means for rotating the expandable implant relative to the pedicle anchor, and for blocking the expandable (Continued)

implant in a predetermined orientation. Methods of deploying the device are also disclosed.

19 Claims, 13 Drawing Sheets

(58) Field of Classification Search
 USPC .......................... 606/66, 297, 310, 326, 327
 See application file for complete search history.

(56) References Cited

U.S. PATENT DOCUMENTS

| | | | |
|---|---|---|---|
| 7,901,409 B2 | 3/2011 | Canaveral et al. | |
| 8,734,497 B2 | 5/2014 | Goel et al. | |
| 8,784,491 B2 | 7/2014 | Biedermann et al. | |
| 8,986,386 B2 | 3/2015 | Oglaza et al. | |
| 9,084,647 B2 | 7/2015 | Suh | |
| 10,603,080 B2 | 3/2020 | Oglaza et al. | |
| 10,821,002 B1 | 11/2020 | Hibri | |

| | | | | |
|---|---|---|---|---|
| 2009/0281628 A1* | 11/2009 | Oglaza | ............... | A61B 17/7065 623/17.15 |
| 2012/0071977 A1 | 3/2012 | Oglaza et al. | | |
| 2012/0109223 A1* | 5/2012 | Biedermann | ...... | A61B 17/7032 606/319 |
| 2012/0116465 A1* | 5/2012 | Elahinia | ............. | A61B 17/8625 606/310 |
| 2012/0123481 A1* | 5/2012 | Lin | .................... | A61B 17/7032 606/301 |
| 2014/0277169 A1 | 9/2014 | Hibri et al. | | |
| 2016/0220275 A1* | 8/2016 | Ratron | ................. | A61B 17/686 |
| 2016/0317188 A1 | 11/2016 | Oglaza et al. | | |
| 2017/0143389 A1 | 5/2017 | Jansen et al. | | |
| 2021/0128316 A1 | 5/2021 | Oglaza et al. | | |
| 2021/0282826 A1* | 9/2021 | Oglaza | .................. | A61F 2/4455 |

FOREIGN PATENT DOCUMENTS

| | | | | | |
|---|---|---|---|---|---|
| WO | WO-2007134248 A1 | * | 11/2007 | ......... | A61B 17/8625 |
| WO | WO-2022025759 A1 | * | 2/2022 | ......... | A61B 17/8685 |

* cited by examiner

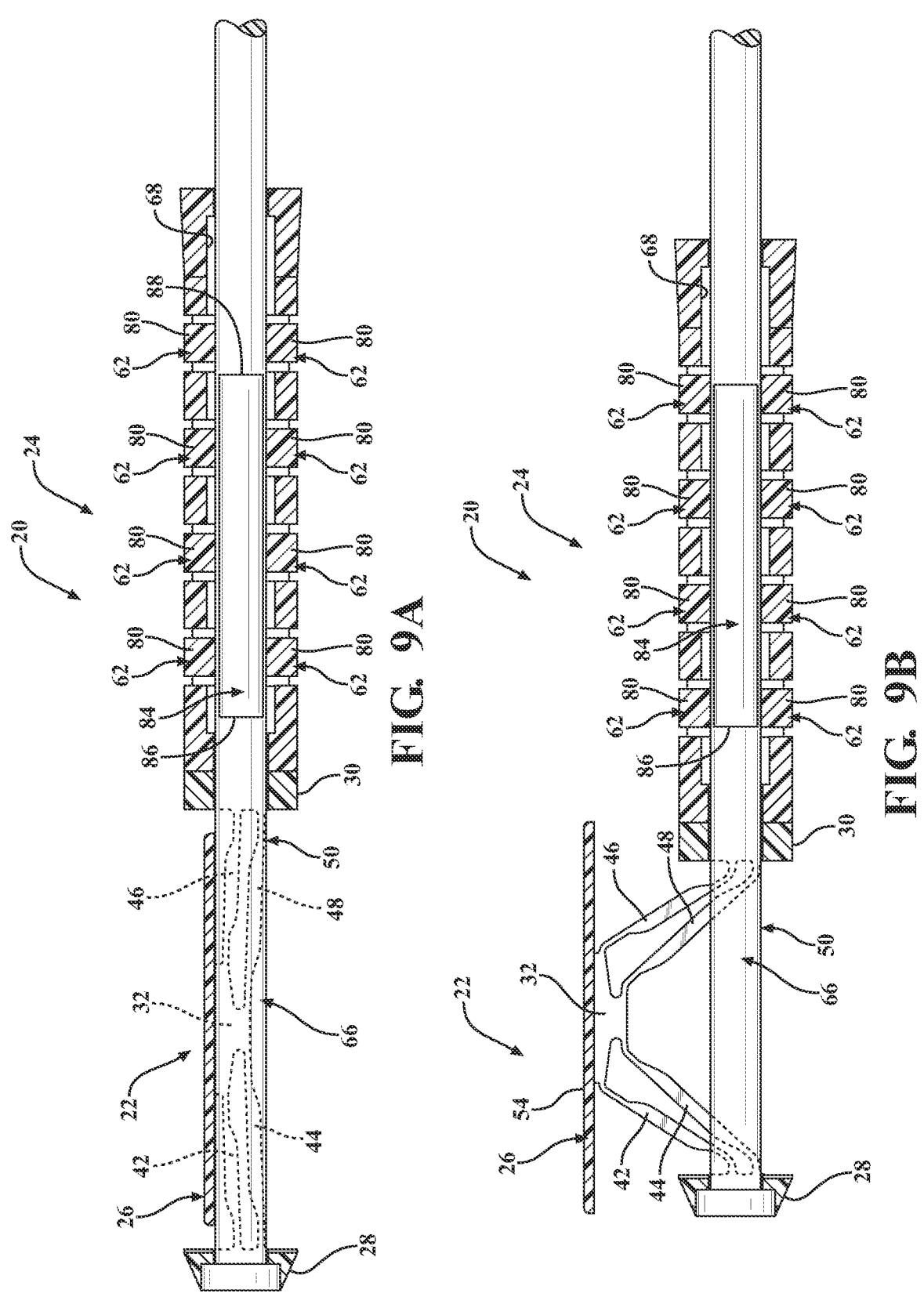

DEVICE INCLUDING AN EXPANDABLE IMPLANT AND ANCHORING ELEMENTS FOR ANCHORING THE DEVICE WITHIN A VERTEBRAL PEDICLE

PRIORITY CLAIM

This application is a national entry of International Application No. PCT/US2022/053335, filed on Dec. 19, 2022, which claims priority to and all the benefits of U.S. Provisional Patent Application No. 63/291,712, filed Dec. 20, 2021, the entire contents of each being hereby incorporated by reference.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly.

A vertebral augmentation procedure is a treatment modality in which the height of the vertebral body is elevated or restored, and stabilized at the elevated or restored height. One manner of doing so includes deploying an implant within the vertebral body. The implant is configured to expand to elevate or restore the height of the vertebral body. The implant may remain within the vertebral body to enhance and maintain structural integrity of the vertebral body at the elevated or restored height. An exemplary implant and system for doing so is described in commonly-owned U.S. Pat. No. 7,846,206, issued Dec. 7, 2010, among others, entire contents of which are hereby incorporated by reference, and sold under the tradename SpineJack by Stryker Corporation (Kalamazoo, Mich.).

As implied by its name, the SpineJack implant includes at least two pairs of supports (or tissue support skis) configured to move upper and lower plates in the caudocranial direction in a scissor jack-like fashion. The implant is deployed through a working cannula, which itself is inserted percutaneously through a vertebral pedicle of the vertebra. The working cannula may be approximately ten, six, or even four gauge, and the implant is correspondingly sized to be less than the inner diameter of the working cannula. Therefore, surfaces of the upper and lower tissue support skis may be arcuate to provide a cylindrical profile to the implant in its collapsed or insertion configuration to be deployed through the working cannula. With the implant capable of providing up to 1,000 Newtons of expansion force, it would be desirable to limit pressure from the arcuate surfaces on the vertebral endplates during expansion to the deployed configuration.

Certain known devices provide for securing an intravertebral implant to the vertebral pedicle. An exemplary system for doing so is described in U.S. Pat. No. 8,784,491, issued Jul. 22, 2014, and commonly-owned U.S. Pat. No. 10,603,080, issued March 31. 2020, entire contents of each being hereby incorporated by reference. Those systems include a pedicle anchor including an external thread configured to be threadably secured to the vertebral pedicle with the implant operably coupled to the pedicle anchor. Yet while the working cannula is tubular, the vertebral pedicle itself is shaped more akin to an oval or ellipse. Therefore, portions of the vertebral pedicle are being underutilized and the maximum permissible implant for a given anatomy is constrained by the cylindrical profile of the external threads of the pedicle anchor.

Therefore, there is a continued need in the art for an intervertebral implant that may be anchored to the vertebral pedicle in a manner to improve treatment of compression fractures and sequelae, and optionally do so without the use of bone cement.

SUMMARY

A device for augmenting a vertebral body of a vertebra. The device is configured to be anchored within a vertebral pedicle and include an expandable implant configured to be deployed within the vertebral body. The anchoring of the device in the vertebral pedicle may obviate the need for bone cement and simplify design of the expandable implant. The device includes an expandable implant, and a pedicle anchor coupled to the expandable implant to support the expandable implant in the desired position. A tissue support ski is moved with deployment of the expandable implant from an insertion configuration to a deployed configuration to compress adjacent cancellous bone and move an upper endplate of the vertebral body to an elevated or restored height. An actuator may extend through the expandable implant and be configured to deploy the expandable implant from the insertion configuration to the deployed configuration.

The expandable implant includes a distal end element, a proximal end element, and struts. The expandable implant may include a strut hub directly connected, secured to, or formed integrally with an underside of the tissue support ski. The struts may be directly connected, secured to, or formed integrally with the strut hub. One, more than one, or all of the struts may include at least one material web that are reduced thickness portions configured to plastically deform as the expandable implant is deployed. The struts may be secured to the distal end element or the proximal end element so as to be angled towards the tissue support ski in the insertion configuration. The angle ensures the struts buckle in the appropriate direction to urge the tissue support ski upwardly away from the longitudinal axis. The struts may be coupled to a lower aspect of the distal end portion or the proximal end portion to provide the necessary clearance to angle the struts. In certain implementations, the expandable implant may include a distal truss secured to the distal end element and the distal strut, and a proximal truss secured to the proximal end element and the proximal strut.

A tissue contact surface of the tissue support ski may be recessed from the outer profile. The tissue contact surface may be offset from the longitudinal axis and define a geometric chord of a cylindrical outer profile of the expandable implant. The tissue contact surface may be partially or entirely planar. The tissue support ski may be moved by an initial lifting approximately equal to the recess prior to encountering the cancellous bone within the vertebral body. The tissue contact surface may be texturized, such as ridges, grooves, dimples, bumps, and the like. Surfaces or subcomponents of the device may be formed from porous material to promote bony ingrowth.

The pedicle anchor includes an anchor body, and at least one anchoring element movably coupled to the anchor body. The anchoring elements are configured to be deployed outwardly beyond the anchor body to engage or penetrate the vertebral pedicle. The anchor body may define a bore, and a rod of the actuator may be movably disposed within the bore. The rod may include knuckles, and the knuckles may be separated by cavities defined by the rod. The anchoring elements are shaped such that an inner edge surface is disposed within the cavities in the insertion configuration, and an outer surface are within the outer profile of the anchor body. The anchoring elements may be integrally formed with the anchor body and include a living hinge formed by a thinned portion of material. The knuckles may be protuberances extending beyond the nominal outer diameter of the rod. A number of the knuckles provided may correspond to the number of the anchoring elements, or one of the knuckles may be configured to deploy an opposing pair of the anchoring elements. The translation of the rod causes the knuckles to engage the inner surfaces of the anchoring elements, and interference between the knuckles and the anchoring elements causes the anchoring elements to pivot or flex outwardly about the living hinge. The knuckles may include at least one tooth or barb configured to be moved into irreversible interference engagement with a complementary feature of the anchoring elements. The anchoring elements centered or radially offset on a longitudinal center plane separating the device into left and right halves. The tissue support ski and the anchoring elements may be moved in a same plane of expansion. The translation of the rod may cause the tissue support ski to be moved away from the longitudinal axis, and therefore the translation of the rod may simultaneously deploy the expandable implant and the pedicle anchor.

In certain implementations, the anchoring elements may include fingers integrally formed with the anchor body. The fingers may be formed by defining slots within the anchor body. The rod of the actuator including a cam extending outwardly from opposing sides of the rod. The cam is configured to be move into engagement with the inner surface of the anchoring elements to move the device from the insertion configuration to the anchored configuration. Interference between the cam and the inner surfaces of the anchoring elements causes the fingers to flex or pivot outwardly beyond the outer profile of the anchor body. The fingers may include edges defined by the slots that are sufficiently sharp to penetrate and engage the vertebral pedicle. Sequential deployment of the expandable implant and the pedicle anchor may include a first input to the actuator to translate the rod to move the expandable implant from the insertion configuration to the deployed configuration, and a second input to rotate the rod to move the pedicle anchor from the insertion configuration to the anchored configuration. With the rod in a first axial position, a cam distal end is positioned distal to the distal-most one of the anchoring elements. The first input to the actuator translates the rod from the first axial position to a second axial position in which the cam is moved into axial alignment with the proximal-most one of the anchoring elements for the second input to rotate the cam to deploy the anchoring elements and move the pedicle anchor to the anchored configuration.

In certain implementations, the distal and proximal end portions may be elliptical or oval to define the outer profile as an oval prism. A width of the expandable implant is greater than its height to form the oval shape. The tissue contact surface may be oriented along or parallel to the width that is greater than the height. The device includes means for rotating the expandable implant relative to the pedicle anchor. The expandable implant may be rotated approximately 90 degrees relative to the pedicle anchor. The expandable implant may include proximal engagement features operably engaging distal engagement features of the pedicle anchor to permit rotation relative to the pedicle anchor in a first rotational direction, and prevent rotation relative to the pedicle anchor in a second rotational direction. The rod of the actuator may include a head portion configured to engage a keyway of the expandable implant to provide for rotation of the expandable implant. The head portion may be non-circular. The device may include a blocking feature to prevent further rotation of the expandable implant in the first rotational direction to greater than a predetermined angle. The predetermined angle may be approximately 90 degrees, or more generally within the range of 80 to 100 degrees. The blocking feature may be protrusions defined a distal end of the bore of the anchor body. The protrusions are radially oriented to interfere with the head portion of the rod when the rod is at the predetermined angle.

BRIEF DESCRIPTION OF THE DRAWINGS

Advantages of the present invention will be readily appreciated as the same becomes better understood by reference to the following detailed description when considered in connection with the accompanying drawings.

FIG. 9A is a sectional elevation view of the device of FIG. 7 taken along section lines 9-9. The expandable implant and the pedicle anchor are in the insertion configuration.

FIG. 9B is a sectional elevation view of the device of FIG. 7. The expandable implant is in the deployed configuration, and the pedicle anchor is in the insertion configuration.

DETAILED DESCRIPTION

Figure 1:
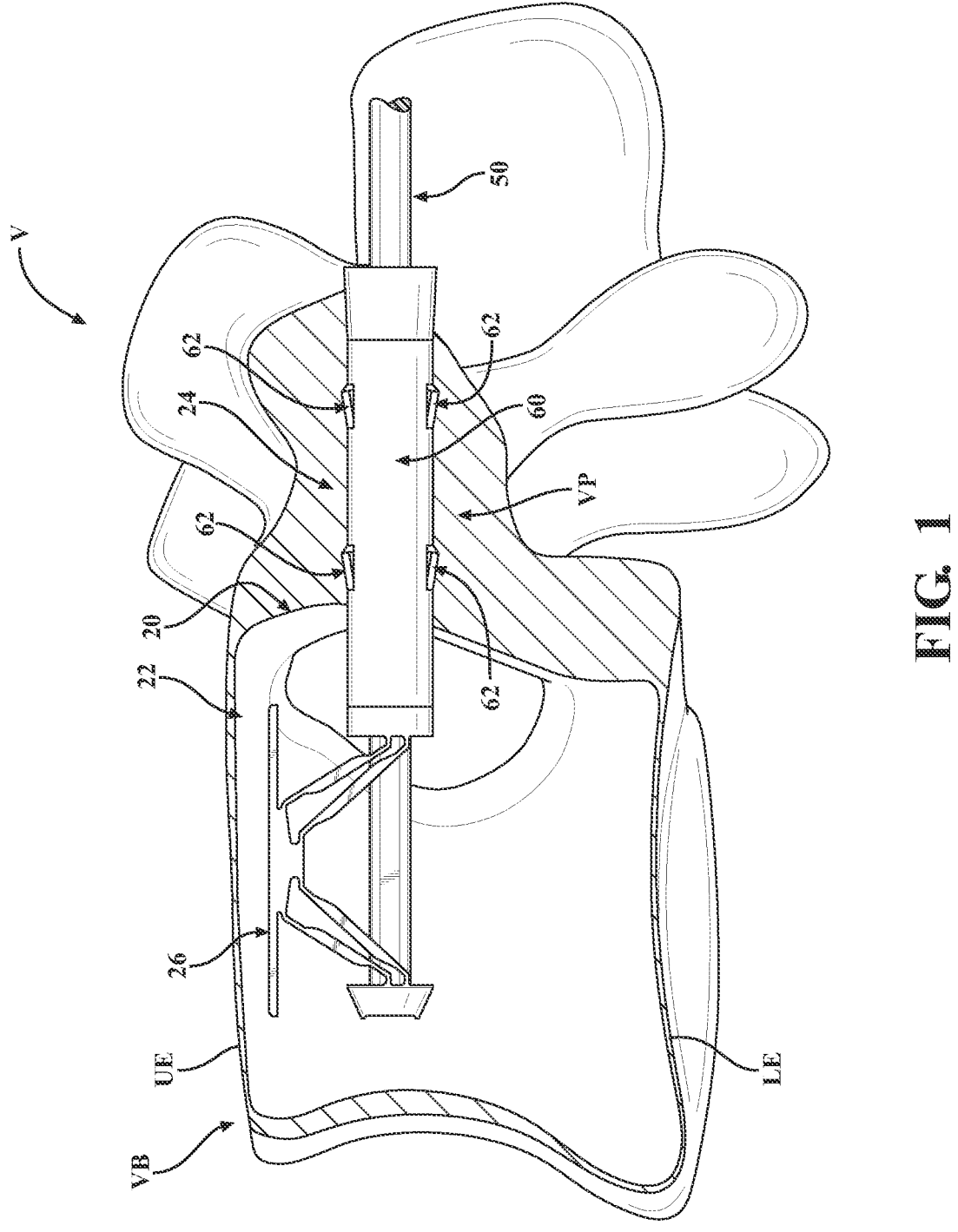
FIG. 1 is a sectional elevation view of a device including an expandable implant deployed within a vertebral body and a pedicle anchor engaged with a vertebral pedicle.
Figure 2:
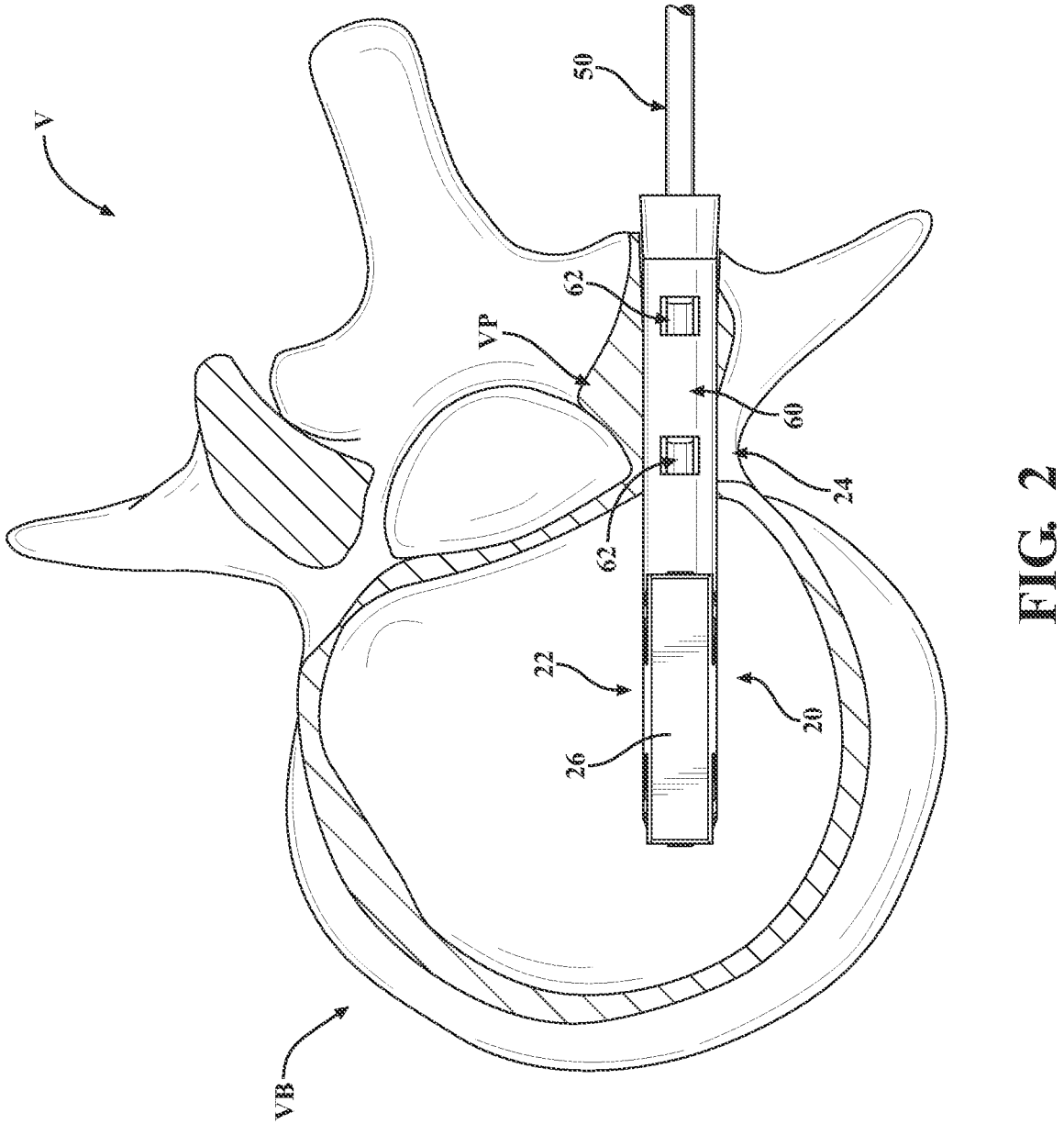
FIG. 2 is a sectional plan view of the device of FIG. 1.

FIGS. 1-3 are illustrations of a device 20 deployed within a vertebra (V) that includes a vertebral body (VB) and a vertebral pedicle (VP). The vertebral body defines an interior region having cancellous bone. The device 20 may be used with a system that includes an access cannula, and an introducer device to which the device 20 is configured to be removably coupled. The device 20 is configured to augment the vertebral body to an elevated or restored height in which at least one endplate of the vertebral body is moved, which may reduce or eliminate pain and other sequelae associated with osteoporotic degeneration, compression fracture, or other related disorder of the spine. An example of the access cannula, introducer device, and other instrumentation suitable for deploying the device 20 is disclosed in commonly-owned U.S. Pat. No. 8,986,386, issued Mar. 24, 2015, the entire contents of which are hereby incorporated by reference. It is noted that anatomical directions may also be referenced in the present disclosure in accordance with standard medical convention; i.e., cranial towards the head of patient or upwardly, caudal towards the feet of the patient or downwardly, distal towards an end of the device inserted first into the patient (or away from the practitioner), and proximal towards the practitioner.

As best shown in FIG. 1, the device 20 includes an expandable implant 22 configured to be deployed in the cranial direction within the interior of the vertebral body to move an upper endplate (UE) away from a lower endplate (LE). The device 20 includes a pedicle anchor 24 coupled to the expandable implant 22 and configured to engage the vertebral pedicle to anchor the device 20. The pedicle anchor 24 supports the expandable implant 22 in the desired position. which may obviate the need for bone cement. In other words, the system including the device 20 may be a cementless system, thereby eliminating cumbersome steps of preparation and administration of the bone cement. A cementless system may also be particularly advantageous to lessen the likelihood of postsurgical complications over the long-term for younger and active individuals with a lifestyle more likely to place dynamic loads on the spine.

The expandable implant 22 includes a tissue support ski 26. The tissue support ski 26 is configured to be moved with deployment of the expandable implant 22 from an insertion configuration to a deployed configuration to be described. The tissue support ski 26 compresses adjacent cancellous bone and moves the upper endplate of the vertebral body to the elevated or restored height. With the pedicle anchor 24 supporting the expandable implant 22 in the desired position, a singular one of the tissue support ski 26 may be used to achieve the desired restoration of height in a cementless system. Predecessor devices that are fully deployed within the vertebral body—i.e., without anchoring to the vertebral pedicle-typically have required a radially deployed implant or opposing skis together with bone cement. In a manner to be described, the use of a single tissue support ski 26 provides for the tissue support ski 26 being recessed from an outer profile of the expandable implant 22, which in turn may provide for a larger loadbearing surface of the tissue support ski 26. The larger loadbearing surface reduces pressure on the upper endplate from the device 20, thereby lessening the likelihood of surgical and postsurgical complications. It is alternatively contemplated that the expandable implant 22 may include a lower strut 49 or a second tissue support ski.

Figure 4:
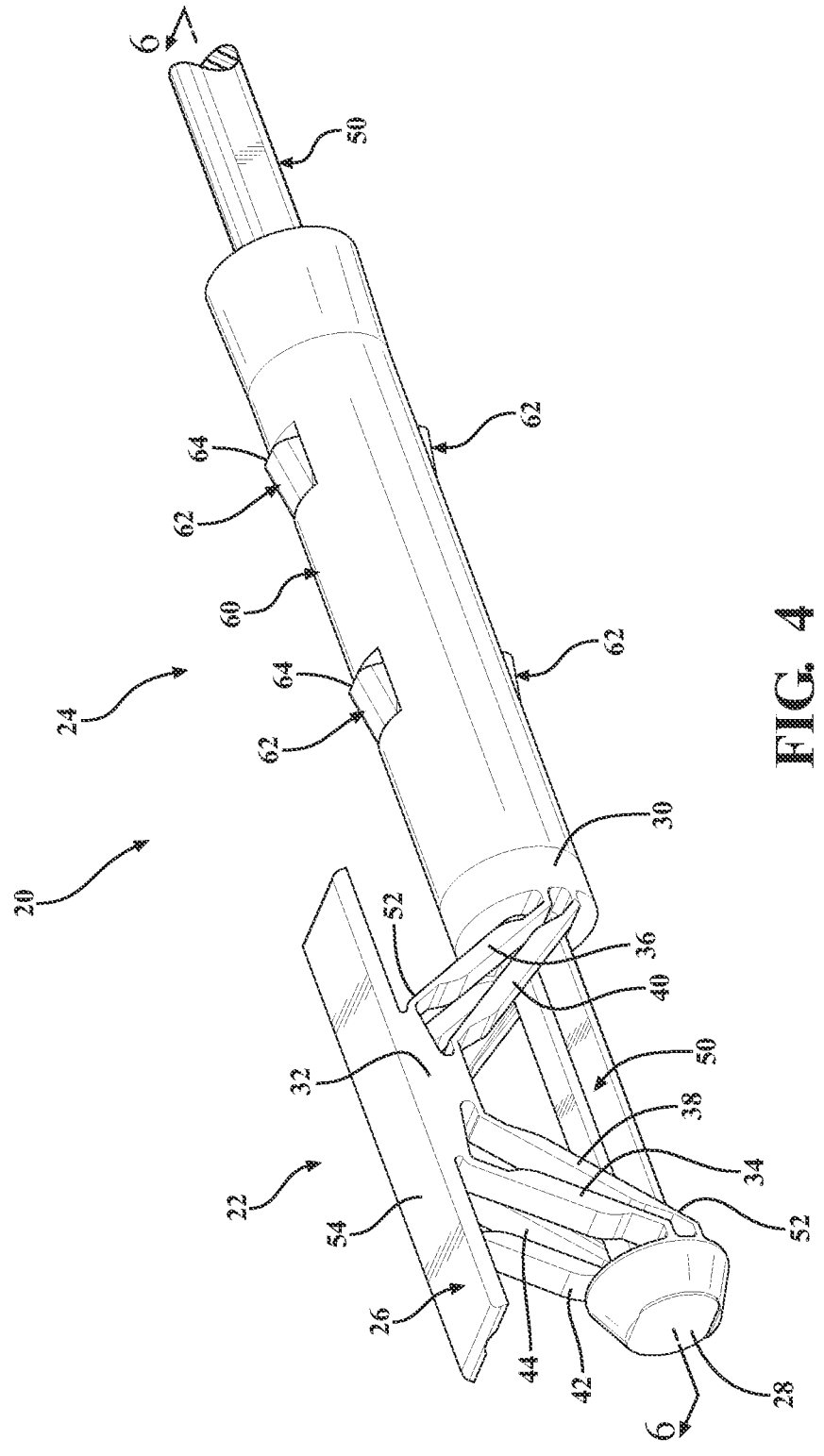
FIG. 4 is a front perspective view of the device of FIG. 1.

With concurrent reference to FIGS. 4-7, the expandable implant 22 includes a distal end element 28 and a proximal end element 30. The distal end element 28 and the proximal end element 30 may define a longitudinal axis of the device 20. The distal end element 28 may define a distal end of the device 20, and the proximal end element 30 may define a proximal end of the expandable implant 22. A distal strut 34 or support is coupled to the distal end element 28 and the tissue support ski 26, and a proximal strut 36 or support is coupled to the proximal end element 30 and the tissue support ski 26. The expandable implant 22 may include a strut hub 32 directly connected, secured to, or formed integrally with an underside of the tissue support ski 26. The distal strut 34 and the proximal strut 36 may be directly connected, secured to, or formed integrally with the strut hub 32. As best shown in FIG. 4, the expandable implant 22 may include several additional struts. A second distal strut 38 may be coupled to the distal end element 28 and the strut hub 32, and a second proximal strut 40 may be coupled to the proximal end element 30 and the strut hub 32. The first distal strut 34 and the second distal strut 38 may be positioned adjacent to and extend along one another between the distal end element 28 and the tissue support ski 26, and the first proximal strut 36 and the second proximal strut 40 may also be positioned adjacent to and extend along one another between the proximal end element 30 and the tissue support ski 26. On a opposite side of an actuator 50 to be described, a mirrored arrangement of struts may be provided. In certain implementations, third and fourth distal struts 42, 44 are coupled to the distal end element 28 and the strut hub 32, and third and fourth proximal struts 46, 48 are coupled to the proximal end element 30 and the strut hub 32.

The struts 34-48 are sized and shaped to impart a desired motion to the tissue support ski 26 during deployment of the expandable implant 22. The actuator 50 is secured to the distal end element 28 and configured to receive an input from the introducer device (via a user) to draw the distal end element 28 towards the proximal end element 30. The struts 34-48 are formed from sufficiently rigid material such that the drawing of the distal end element 28 towards the proximal end element 30 articulates the struts 34-48 in a manner to urge the tissue support ski 26 upwardly away from the longitudinal axis of the device 20. One, more than one, or all of the struts 34-48 may include at least one material web 52 (several identified throughout the figures) that are reduced thickness portions configured to plastically deform as the expandable implant 22 is deployed within the vertebral body. In other words, a thickness of a portion of the struts 34-48 is greater than the thickness of the material webs 52 such that, as the expandable implant 22 is moved from the insertion configuration to the deployed configuration, stresses are localized to impart bending of the material webs 52. The effect of the bending is articulation of the distal struts 34, 38, 42 and 44 relative to each of the distal end element 28 and the tissue support ski 26, and articulation of the proximal struts 36, 40, 46, 48 relative to each of the proximal end element 30 and the tissue support ski 26. The expandable implant 22 may be symmetrical about a plane transverse to the longitudinal axis, and therefore counterpart distal and proximal struts articulate complementarily to cause the tissue support ski 26 to be parallel to the longitudinal axis of the device 20 in both the insertion configuration and the deployed configuration, and possibly during all movement therebetween.

Figures 11, 12A:
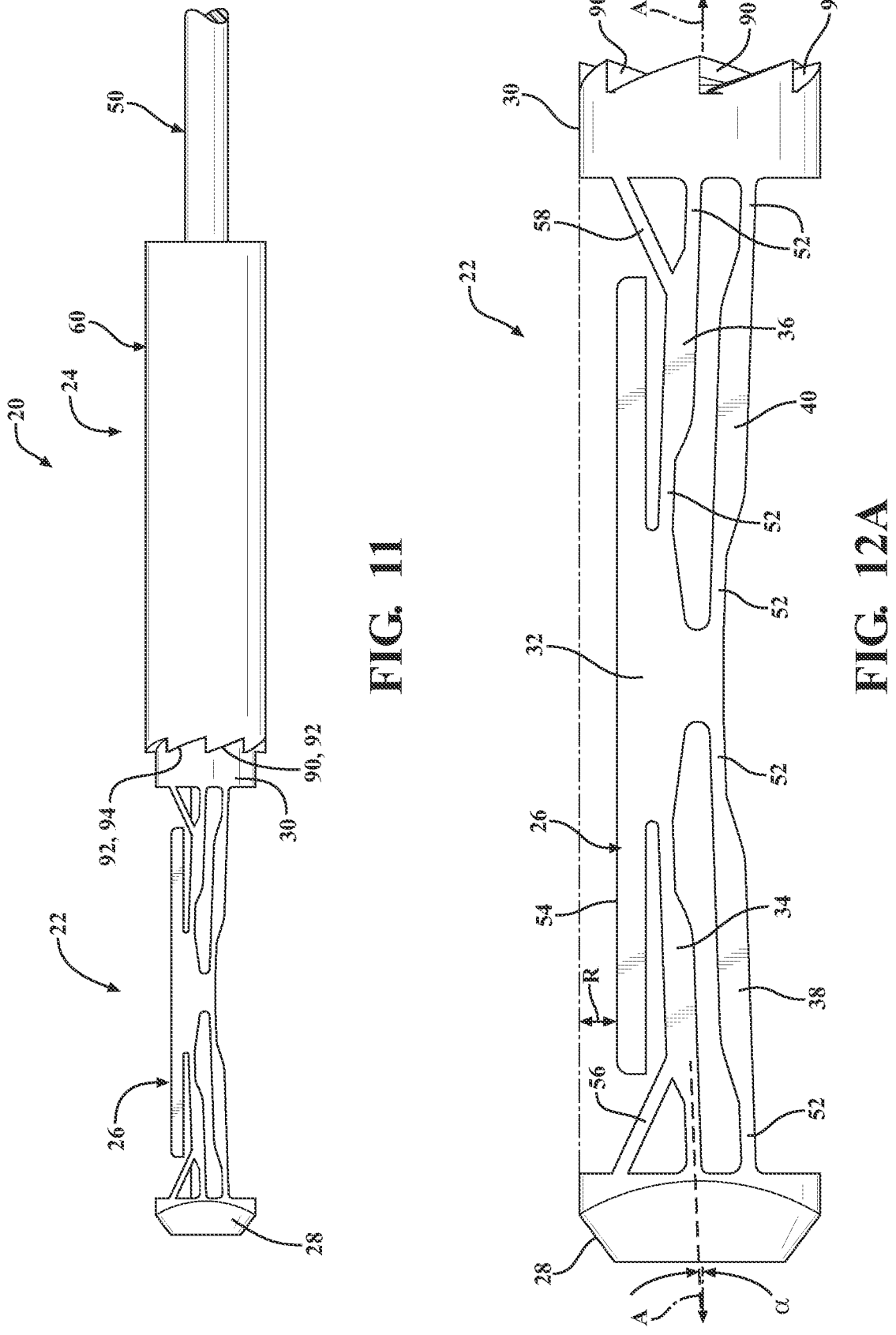
FIG. 11 is an elevation view of the device of FIG. 10 with the expandable implant rotated relative to the pedicle anchor after insertion of the expendable implant.
FIG. 12A is an elevation view of the expandable implant of the device of FIG. 11.
Figure 12B:
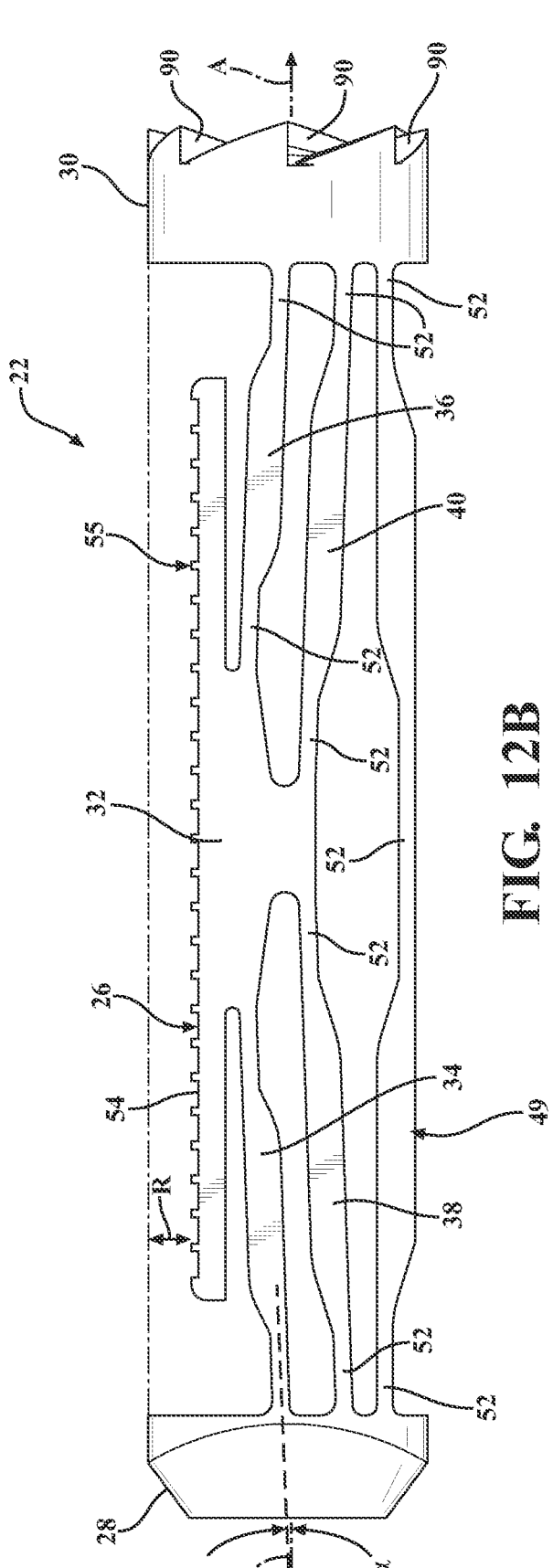
FIG. 12B is an elevation view of another expandable implant of the device of FIG. 11.

As best appreciated from FIGS. 12A and 12B, the struts 34-48 may be secured to the distal end element 28 or the proximal end element 30 so as to be angled towards the tissue support ski 26 in the insertion configuration. The first distal strut 34 is shown as oriented at an angle, α, relative to the longitudinal axis (A) of the expandable implant 22. A same or different angle may be provided for the remaining struts 36-48. The angle, however slight, is sufficient to ensure the struts 34-48 buckle in the appropriate direction to urge the tissue support ski 26 upwardly away from the longitudinal axis. The angle may be between 1 and 10 degrees, and more particularly between 1 and 5 degrees. The use of a single tissue support ski 26 may provide the necessary clearance to angle the struts 34-48 in the afor-mentioned manner. More particularly, to provide for the angling of the struts 34-48 in the insertion configuration, the struts 34-48 may be coupled to a lower aspect of the distal end element 28 or the proximal end element 30, which may otherwise be unfeasible in an implant with a second tissue support ski requiring its own associated struts. For example, FIGS. 12A and 12B show ends of the first distal and proximal struts 34, 36 coupled to a respective one of the distal and proximal end elements 28, 30 along the longitu-dinal axis, and ends of the second distal and proximal struts 38, 40 coupled to a respective one of the distal and proximal end elements 28, 30 opposite the longitudinal axis from the tissue support ski 26 (i.e., the lower aspect of the distal end element 28 or the proximal end element 30). Knowing that the tissue support ski 26 should not extend beyond the outer profile of the device 20 in the insertion configuration, the relatively lower coupling points of the struts 34-48 provides clearance for not only the upward angling of the struts 34-48 in view of such a constraint, but also a recess (R) of the tissue support ski 26 from the outer profile of the device 20.

Figure 10:
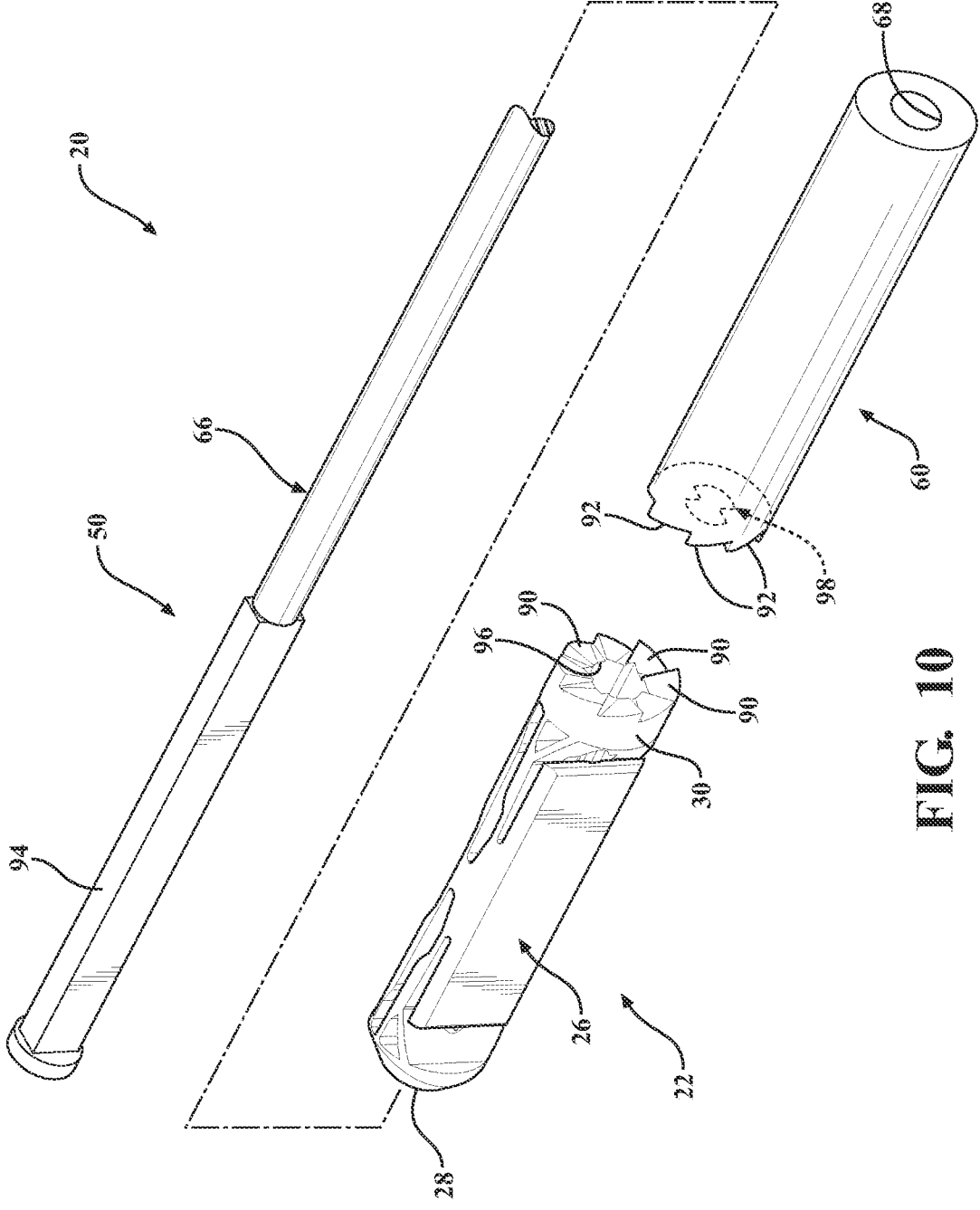
FIG. 10 is an exploded view of another implementation of the device.
Figure 13:
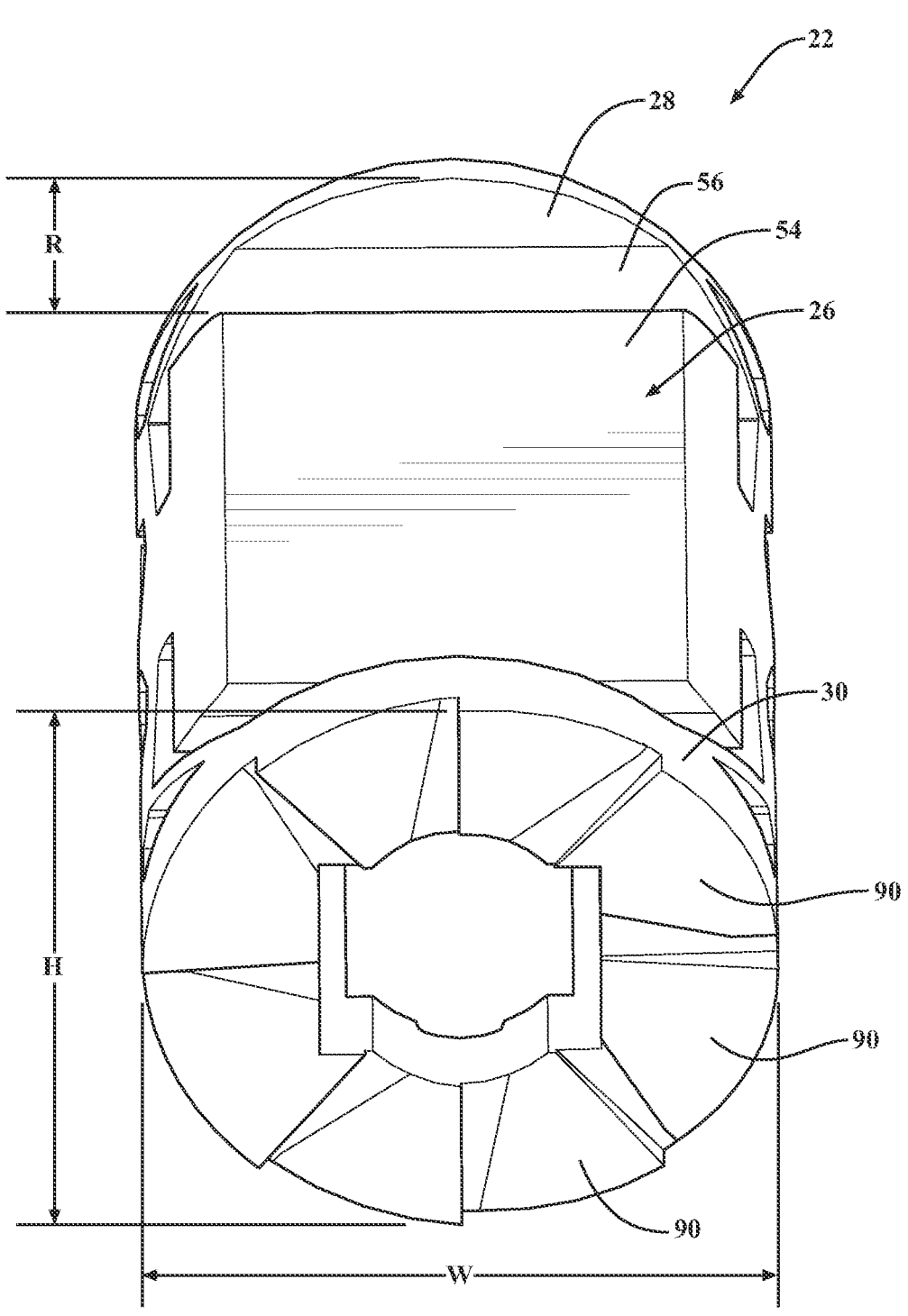
FIG. 13 is a top perspective view of the expandable implant of FIG. 12A.

With continued reference to FIG. 12A and further refer-ence to FIG. 13, the tissue support ski 26 may include an upper or tissue contact surface 54 opposite its underside. The distal end element 28 may at least include a cylindrical portion, and the proximal end element 30 may be cylindri-cal. For convention, the outer profile of the expandable implant 22 may be a cylinder defined by the cylindrical portion of the distal end element 28 and the cylinder of the proximal end element 30—the dashed line in FIG. 12A represents an upper aspect of the outer profile. It is alterna-tively contemplated that the distal and proximal end ele-ments 28, 30 may be elliptical or oval to define the outer profile as an oval prism. FIG. 13 shows one such imple-mentation in which a width (W) of the expandable implant 22 is greater than its height (H) to form the oval shape. The tissue contact surface 54 of the tissue support ski 26 is recessed (R) from the outer profile. For example, the tissue contact surface 54 may be offset from the longitudinal axis and define a geometric chord of the cylindrical outer profile of the expandable implant 22. The technical advantages of the tissue contact surface 54 being recessed from the outer profile are at least fourfold. First, the tissue contact surface 54 may be partially or entirely planar. FIG. 13 shows the tissue contact surface 54 as entirely planar and rectangular in shape. Second, the tissue contact surface 54 may be relatively larger. In other words, a greater portion of a width of the expandable implant 22 may be utilized as the tissue contact surface 54. This is especially the case in implemen-tations where the expandable implant 22 is oval-shaped. In other words, the tissue contact surface 54 of the expandable implant 22 of FIGS. 10 and 13 is wider than the tissue contact surface 54 of the expandable implant 22 of FIGS. 4 and 7. Since pressure is a force per unit area, the planar and larger tissue contact surface 54 reduces pressure on the upper endplate both during deployment of the device 20 and once in situ. The reduced pressure permits larger forces to be applied to the upper endplate, thereby realizing greater restoration of height with less concern for endplate com-promise. Once in situ, greater static and dynamic forces on the upper endplate from the tissue contact surface 54 may be endured without increasing focal pressure, thereby provid-ing a more robust device. Third, the tissue support ski 26 may be moved by an initial lifting approximately equal to the recess (R) prior to encountering the cancellous bone within the vertebral body. The initial lifting provides for greater mechanical advantage from the insertion tool once resistance from the cancellous bone is encountered. Further, the subsequent encountering of the cancellous bone may be felt by the surgeon as tactile feedback, and thus the surgeon can distinguish between internal resistance from the expand-able implant 22 itself and the resistance from the cancellous bone. Fourth, the tissue contact surface 54 may be texturized for improved engagement with the upper endplate and to promote bony ingrowth. For example, the tissue contact surface 54 may include ridges, grooves, dimples, bumps, and the like, generally represented at 55 in FIG. 12B. Additionally or alternatively, the tissue contact surface 54 and/or any of the surfaces of the device 20 may be formed from porous material to promote bony ingrowth.

It should be appreciated that any and all of the aformen-tioned features of the expandable implant 22 described with reference to FIG. 12A are or may be included on the other implementations of the expandable implant 22 described herein. The implementation of the expandable implant 22 of FIG. 12A may further include a distal truss 56 secured to the distal end element 28 and the distal strut 34, and a proximal truss 58 secured to the proximal end element 30 and the proximal strut 36. Owing to the aformentioned lower cou-pling points between the struts 34-48 along the distal and proximal end elements 28, 30, the distal and proximal trusses 56, 58 are configured to prevent outward flaring of the distal and proximal end elements 28, 30 during deploy-ment of the expandable implant 22. In other words, as the distal end element 28 is drawn toward the proximal end element 30 against resistance from the cancellous bone and internal resistance of the expandable implant 22 itself, forces on lower portions of the distal and proximal end elements 28, 30 (e.g., from the struts 34-48) may undesirably cause upper portions of the distal and proximal end elements 28, 30 to flare outwardly. The distal and proximal trusses 56, 58 distribute the forces in a manner to maintain parallel align-ment between the distal and proximal end elements 28, 30. The implementation of the expandable implant 22 of FIG. 12B may further include the lower strut 49. The lower strut 49 may include opposing ends coupled to a respective one of the distal end element 28 and the proximal end element 30. The lower strut 49 may include the material webs 52 sized and shaped to impart movement of the lower strut 49 away from the longitudinal axis in a direction opposite of the tissue support ski 26. The lower strut 49 may provide for added stability of the expandable implant 22 in situ without requiring the clearance needed to provide for a second tissue support ski and its associated struts.

As mentioned, the device 20 includes the pedicle anchor 24 configured to be anchored in the vertebral pedicle. Returning to FIGS. 1-6, the pedicle anchor 24 includes an anchor body 60, and at least one anchoring element 62 movably coupled to the anchor body 60. Plural anchoring elements 62 will be described, but a single one may be provided. The anchoring elements 62 are configured to be deployed outwardly beyond the anchor body 60 to engage the vertebral pedicle, as shown in FIGS. 1-3A. The anchor-ing elements 62 may include a point, edge, corner, or the like, shaped sufficiently to penetrate the cortical bone of the vertebral pedicle. For example, the anchoring elements 62 may include a trailing edge 64 configured to engage the cortical bone and prevent movement of the device 20 relative to the vertebra, and in particular prevent "pull out" of the device 20 once anchored.

Figures 5, 6:
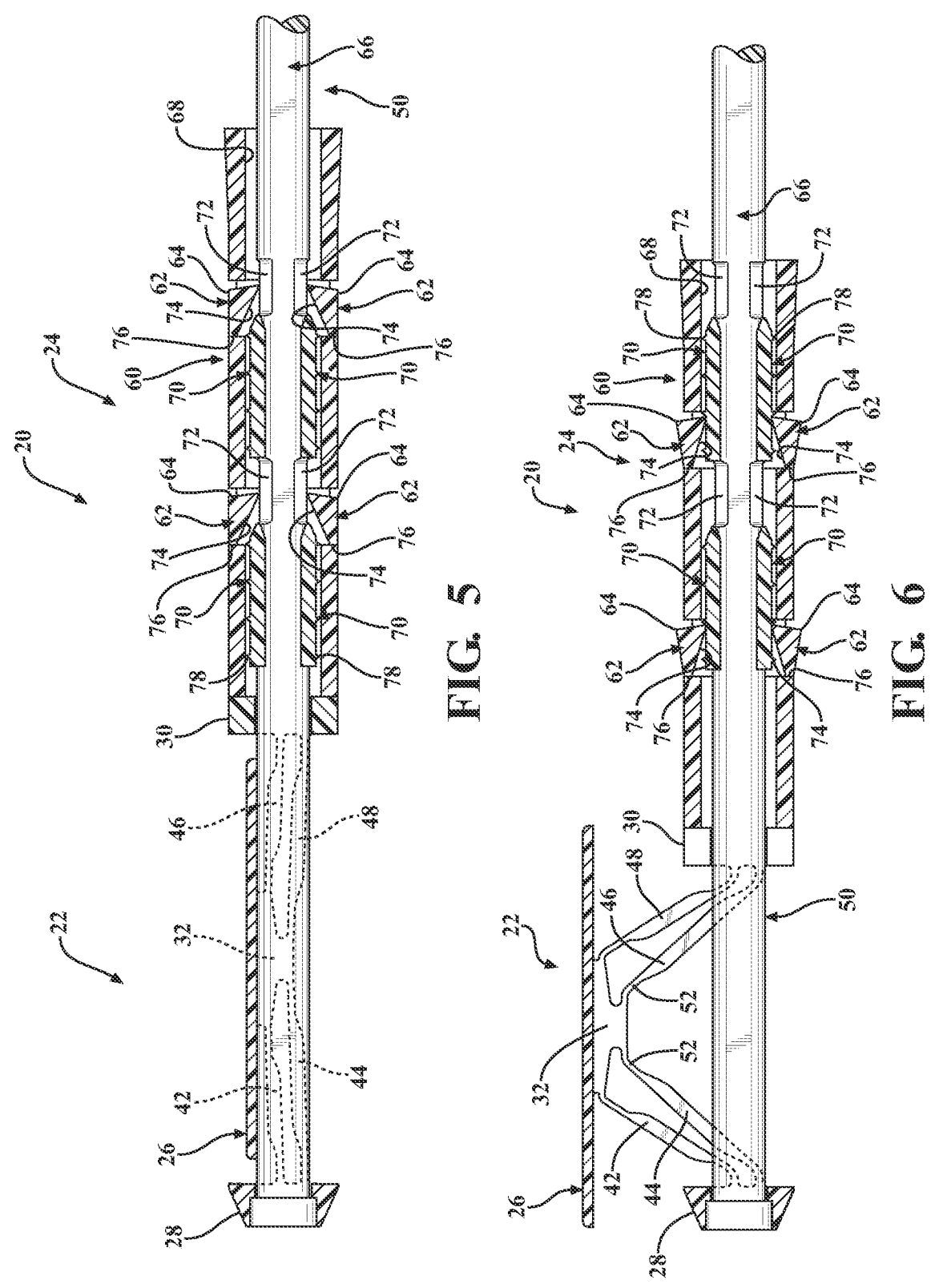
FIG. 5 is a sectional elevation view of the device of FIG. 4 in an insertion configuration.
FIG. 6 is a sectional elevation view of the device of FIG. 4 taken along section lines 6-6. The device is in a deployed configuration.
Figure 7:
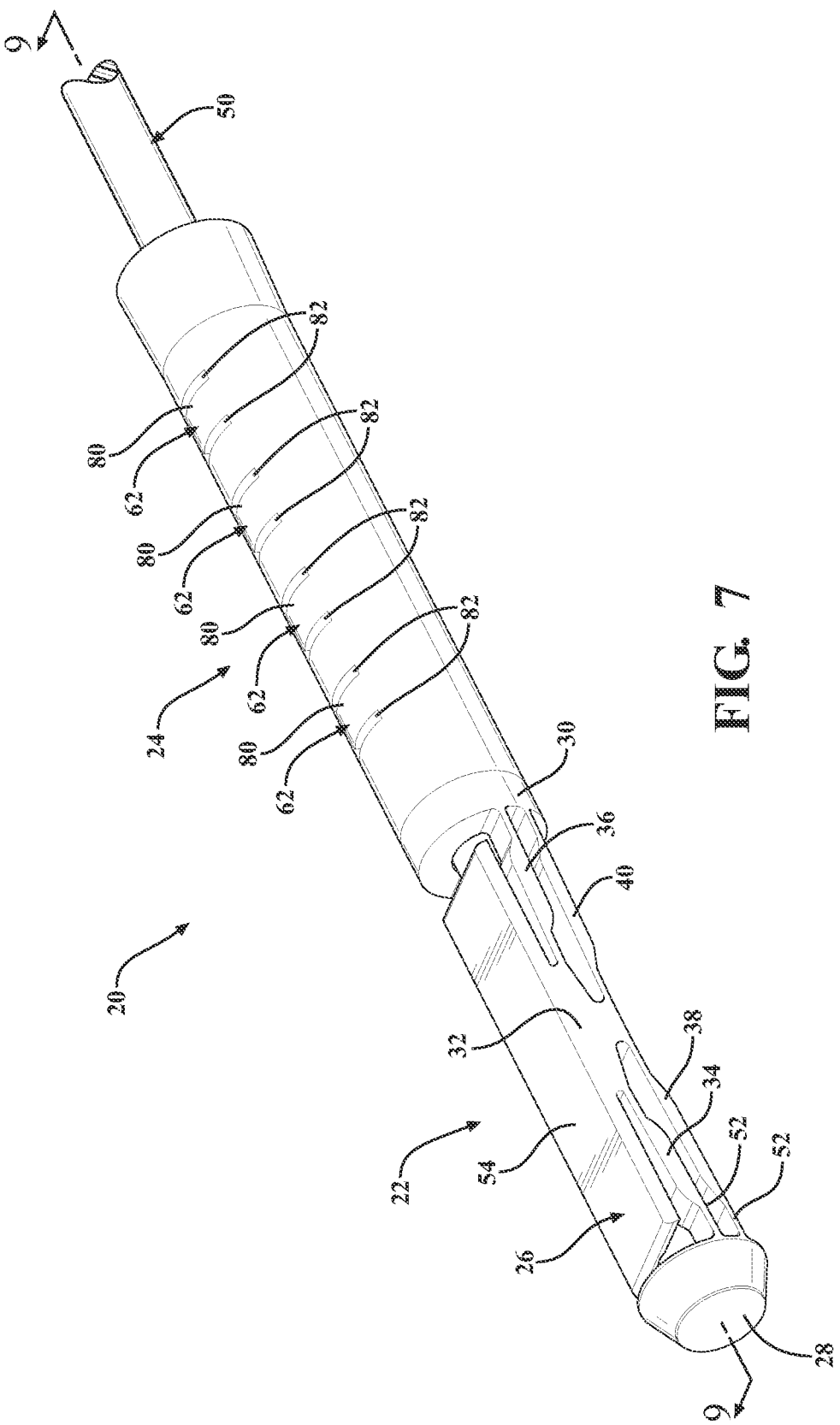
FIG. 7 is a front perspective view of another implementation of the device.
Figure 8:
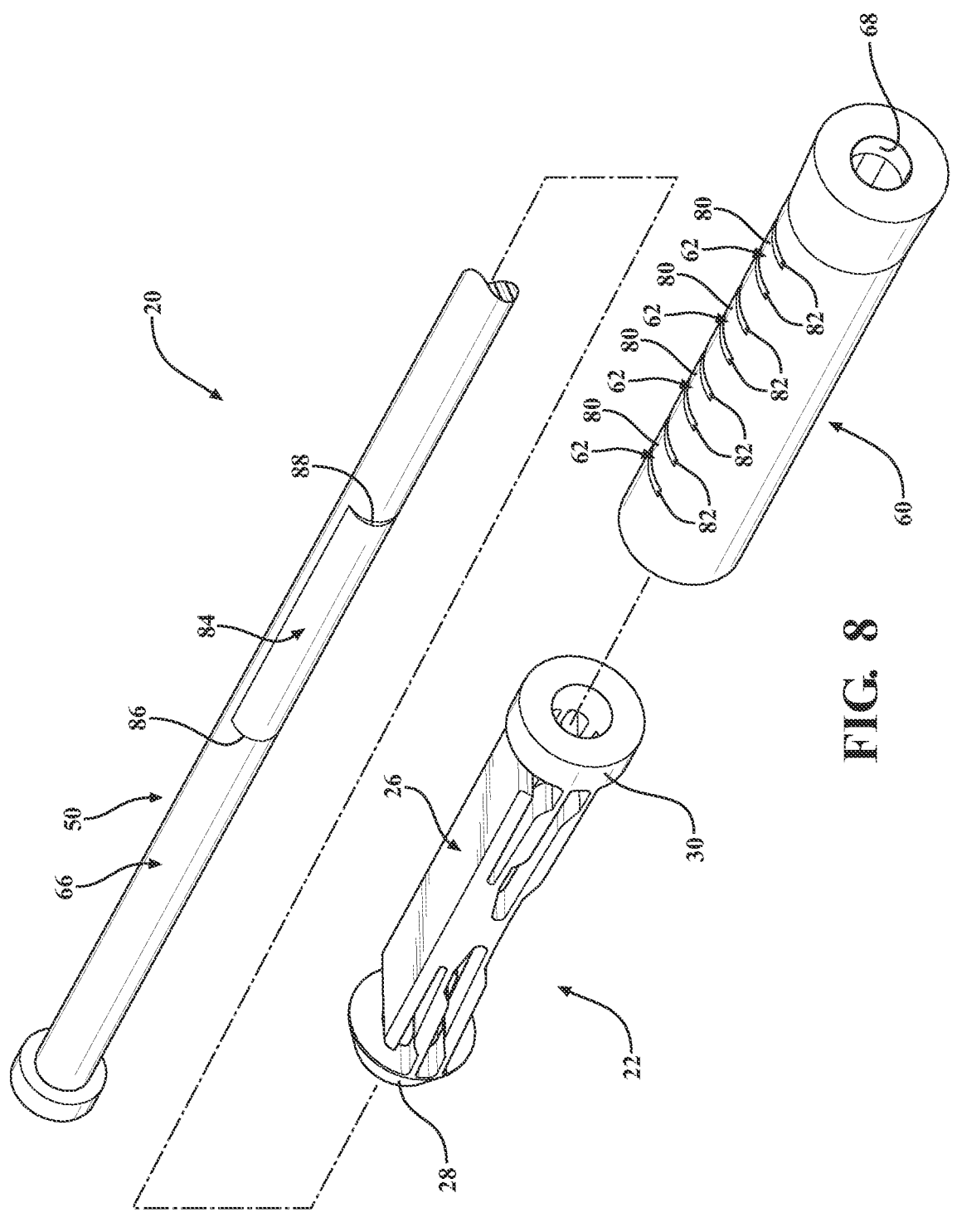
FIG. 8 is an exploded view of the device of FIG. 7.

FIG. 5 shows the device 20 in the insertion configuration in which the tissue support ski 26 and the anchoring elements 62 are positioned within the outer profile of the device 20. FIG. 6 shows the device 20 in the deployed configuration in which the tissue support ski 26 has been moved upwardly, and an anchored configuration in which the anchoring elements 62 have been moved outwardly beyond the anchor body 60. To move the device 20 between the insertion configuration and the deployed configuration, an input is provided to the actuator 50. The actuator 50, which may include a rod 66 removably coupled to the introducer device (not shown), may be translated to draw the distal end element 28 towards the proximal end element 30. The proximal end element 30 may be coupled to or abutting a distal end of the anchor body 60, and therefore the anchor body 60 resists the proximal end element 30 from moving in a corresponding manner. The compressive forces from the distal and proximal end elements 28, 30 are transmitted to the struts 34-48, and the localized stresses cause the material webs 52 to buckle and articulate the struts 34-48 to move the tissue support ski 26 away from the longitudinal axis.

The anchor body 60 may define a bore 68, and the rod 66 may be movably disposed within the bore 68. The rod 66 may include knuckles 70, and the knuckles 70 may be separated by cavities 72 defined by the rod 66. The anchoring elements 62 are shaped such that an inner edge or inner surface 74 are disposed within the cavities 72 in the insertion configuration, and an outer surface including the trailing edge 64 are within the outer profile of the anchor body 60. The anchoring elements 62 may be movably coupled to the anchor body 60 in any one of several suitable arrangements. For example, the anchoring elements 62 may be integrally formed with the anchor body 60 and include a living hinge 76 formed by a thinned portion of material. For another example, the anchoring elements may be coupled to the anchor body 60 with a pivot pin or the like. The knuckles 70 may be protuberances extending beyond the nominal outer diameter of the rod 66. A number of the knuckles 70 provided may correspond to the number of the anchoring elements 62, or one of the knuckles 70 may be configured to deploy an opposing pair of the anchoring elements 62. FIGS. 5 and 6 show four anchoring elements 62 (two movably disposed on an upper aspect of the anchor body 60, and two movably disposed on a lower aspect of the anchor body 60), and two knuckles 70—more or less of either may be provided.

To move the device 20 between the insertion configuration and the anchored configuration, the input is provided to the actuator 50 to translate the rod 66. In the present implementation, the input may be the same input as that to deploy the expandable implant 22, and therefore the expandable implant 22 and the anchoring elements 62 may be deployed at least near simultaneously. The translation of the rod 66 causes the knuckles 70 to engage the inner surfaces 74 of the anchoring elements 62, and interference between the knuckles 70 and the anchoring elements 62 causes the anchoring elements 62 to pivot or flex outwardly about the living hinge 76, thereby penetrating the vertebral pedicle with the trailing edge 64. The knuckles 70 may include at least one tooth or barb 78 configured to be moved into irreversible interference engagement with a complementary feature of the anchoring elements 62. In particular, in the anchored configuration, the barbs 78 are in interference engagement with edges of the inner surfaces 74 of the anchoring elements 62. As a result, the rod 66 may not translate distally relative to the anchor body 60, which would otherwise permit the anchoring elements 62 to pivot or flex inwardly and compromise the anchoring effect. It should be understood that, depending on the design of the cavities 72 relative to the anchoring elements 62, the knuckles 70 may be optional. In other words, should the cavities 72 be sufficient deep to receive the anchoring elements 62 being sufficiently large, the outer surface of the rod 66 itself may provide the desired effect to deploy the anchoring elements 62.

Figures 3A, 3B:
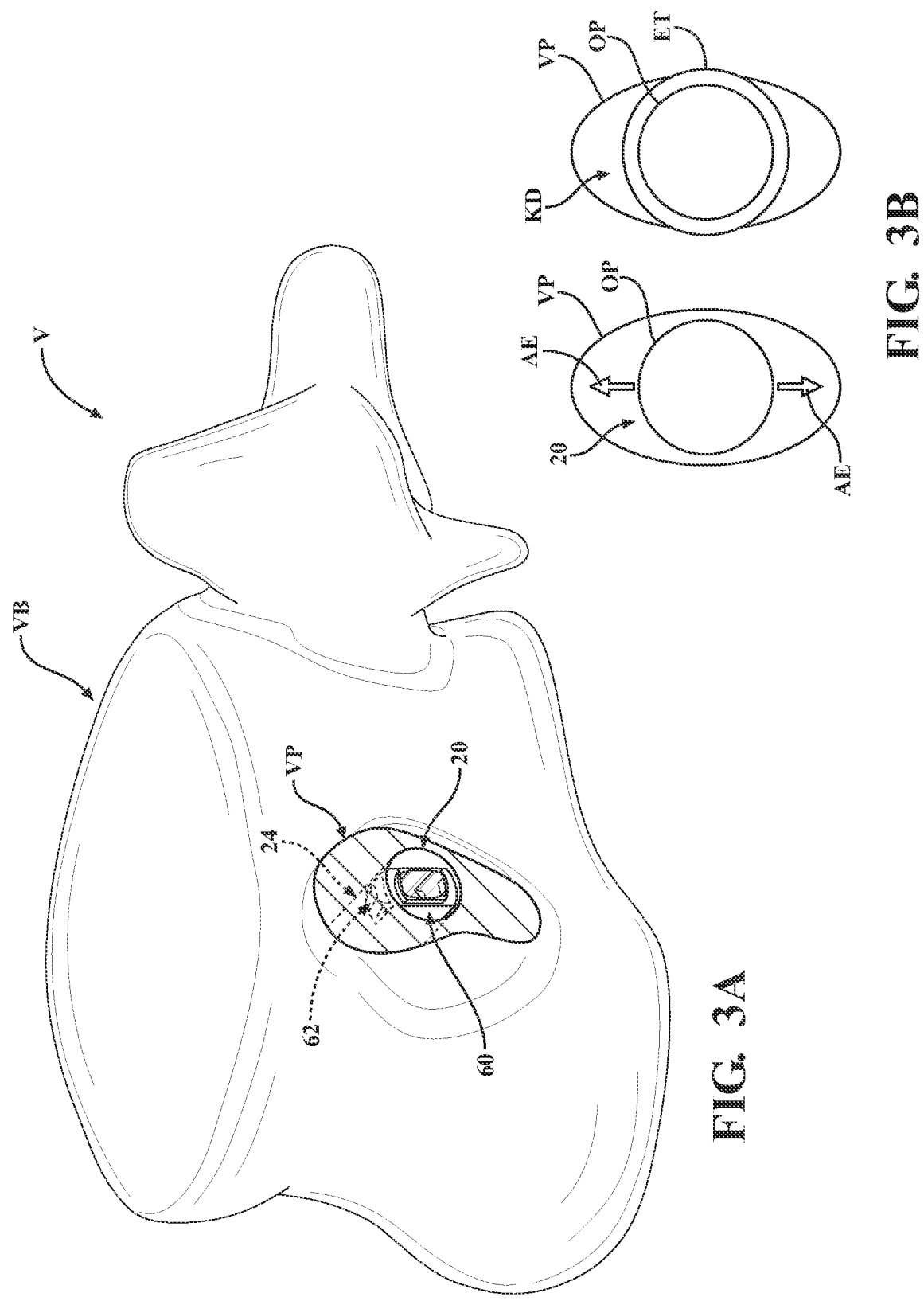
FIG. 3A is a rear perspective sectional view of the device of FIG. 1 in which anchoring elements of the pedicle anchor are deployed generally along the largest dimension of the vertebral pedicle.
FIG. 3B are schematic representations of the device of the present disclosure and a known device overlaid on a representation of the vertebral pedicle. A larger implant for a given vertebral pedicle may be used by orienting the anchoring elements in the caudocranial direction as opposed to an external thread.

As mentioned, the anchoring elements 62 may be arranged on the upper and lower aspects of the anchor body 60. The arrangement realizes a technical advantage over predecessor devices that use external threading to engage the vertebral pedicle. FIG. 3A shows a sectional perspective view of the vertebral pedicle, and it is readily appreciated that the vertebral pedicle is noncircular. In particular, the vertebral pedicle is most closely elliptical or oval in shape, which is schematically represented as vertebral pedicles (VP) in FIG. 3B. The right-sided schematic of FIG. 3B is a representative known device (KD) having an outer profile (OP) and external threads (ET), and the left-sided schematic is the device 20 having the outer profile and anchoring elements (AE). For a given vertebral pedicle, the known device is unable to accommodate the same size outer profile as the device 20 of the present disclosure, as the external threads encroach on the outer surface of the vertebral pedicle. Consequently, the known device, including its expandable portion, would need to be smaller to conform the vertebral pedicle—and the smaller expandable portion of the known device may be insufficient to augment the vertebral body to the desired restored height. By contrast, the anchoring elements of the device 20 provide for a larger outer profile without encroaching on the outer surface of the vertebral pedicle. Stated simply, the device 20 advantageously utilizes more of the available anatomical shape of the vertebral pedicle to provide for the option of larger working cannulas and therefore larger expandable implants.

The illustrated implementations of the device 20 include the anchoring elements 62 centered on a longitudinal center plane separating the device 20 into left and right halves. In such an arrangement, the tissue support ski 26 and the anchoring elements 62 are configured to be moved in a same plane of expansion. For example, the tissue support ski 26 may be deployed cranially, and the anchoring elements 62 may be deployed caudocranially. It should be appreciated, however, that variations in the radial orientation of one or more of the anchoring elements 62 is contemplated. While the anchoring elements 62 may typically be disposed on the upper and lower aspects of the anchor body 60, the anchoring elements 62 may be radially offset from the longitudinal center plane. Based on anatomical shape of the vertebral pedicle, whether the individual patient or a survey of anthropomorphic data, it may be desirable to move one or more of the anchoring elements 62 from the longitudinal center plane by 3, 5, 10 or 15 or more degrees. In one example, after analyzing anatomical shape of the vertebral pedicle for an individual patient on a computed tomography scan in which the specific dimensions may be determined, the surgeon may choose one of the devices 20 from a catalogue of many each having different arrangements of the anchoring elements 62. The one selected may be best suited along the largest dimensions of the vertebral pedicle. In alternative implementations, the anchoring elements 62 may be in a triangular, cruciform, stellate, pentagonal, hexagonal, or another geometric arrangement. Alternatively, portions of the anchoring elements 62 may be frangible and configured to break from the anchor body 60 during deployment. Such an example may include three-dimensionally printing the anchor body 60 with the frangible sections. A further alternative includes an outer surface of the anchoring elements 62 being formed with threads and/or other geometries to facilitate removal of the device 20 should it be indicated to do so.

Referring now to FIGS. 7-9C, another implementation of the device 20 is shown in which the anchoring elements 62 and their mechanism of deployment differs from that previously described. The expandable implant 22 may be similar to or the same as that previously described, and is incorporated herein by reference. The anchoring elements 62 may include fingers 80 integrally formed with the anchor body 60. The fingers 80 are movably coupled to the anchor body 60. The fingers 80 may be formed by defining slots 82 within the anchor body 60. The illustrated implementation shows the slots 82 being U-shaped to define three sides of the fingers 80 and provide a living hinge or material web as the fourth side. Further, the illustrated implementation shows four of the fingers 80 disposed on the upper aspect of the anchor body 60, and four of the fingers 80 disposed on the lower aspect of the anchor body 60. More or less of the fingers 80 may be provided, and the fingers 80 may be disposed on or radially offset from the longitudinal center plane as previously described.

Figure 9C:
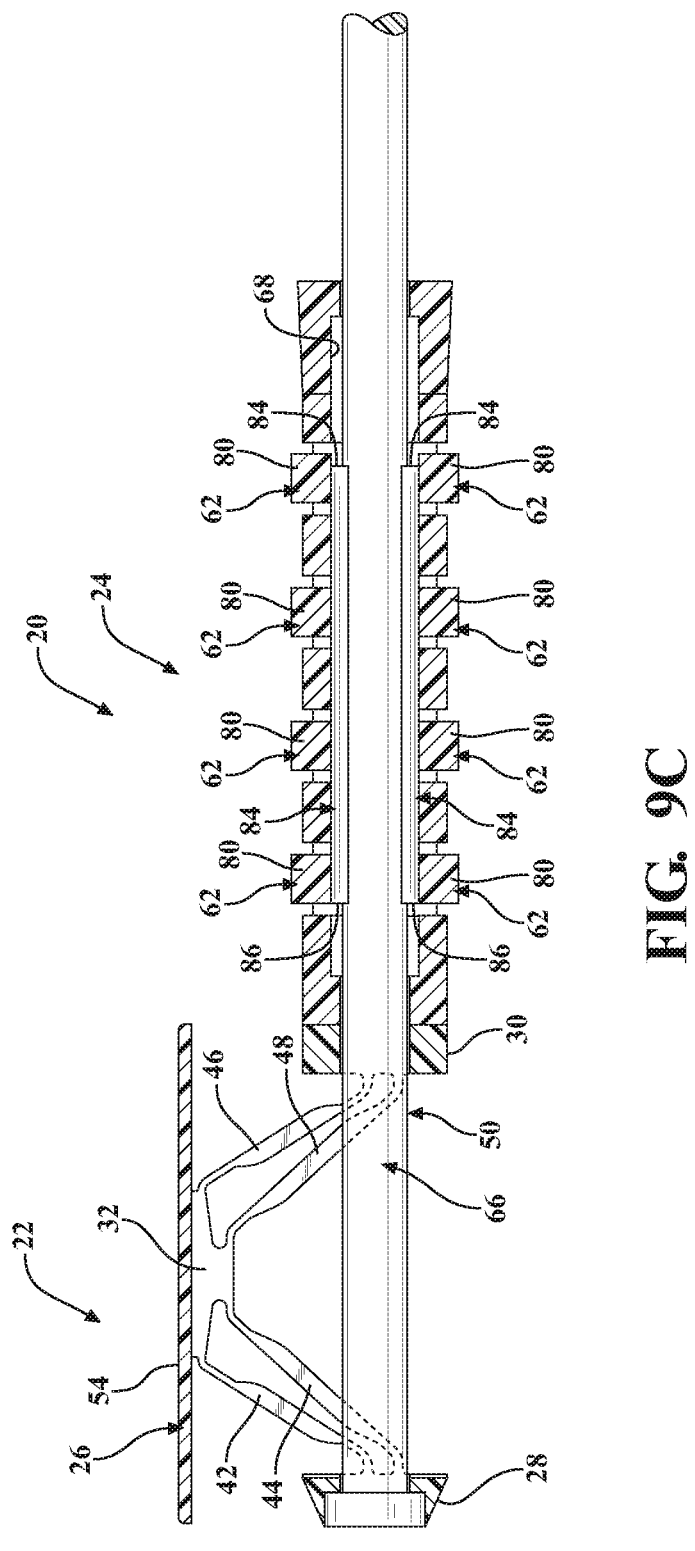
FIG. 9C is a sectional elevation view of the device of FIG. 7. The expandable implant and the pedicle anchor are in the deployed configuration.

FIGS. 8 and 9A-9C show the rod 66 of the actuator 50 including a cam 84. In particular, a portion of the rod 66 may include the cam 84 extending outwardly from opposing sides (one shown) of the rod 66. The cam 84 is configured to be move into engagement with the inner surface 74 of the anchoring elements 62 to move the device from the insertion configuration to the anchored configuration. As best shown in FIG. 9A and 9C, with the rod 66 in a first rotational orientation, the cam 84 is oriented laterally and the nominal outer diameter of the rod 66 is smaller than an inner diameter defined by the inner surfaces 74. The rod 66 is configured to be moved from the first rotational orientation to a second rotational orientation in which the cam 84 is oriented upwardly and downwardly. Interference between the cam 84 and the inner surfaces 74 of the anchoring elements 62 causes the fingers 80 to flex or pivot outwardly beyond the outer profile of the anchor body 60. The fingers 80 may include edges defined by the slots 82 that are sufficiently sharp to penetrate and engage the vertebral pedicle.

The present implementation of the device 20 provides for sequential deployment of the expandable implant 22 and the pedicle anchor 24. Two separate inputs may be provided to the actuator 50, a first input to translate the rod 66 to move the expandable implant 22 from the insertion configuration to the deployed configuration, and a second input to rotate the rod 66 to move the pedicle anchor 24 from the insertion configuration to the anchored configuration. The sequential deployment advantageously provides for confirming positioning of the expandable implant 22 in the deployed configuration prior to (or after) anchoring the device to the vertebral pedicle. In other words, the surgeon may deploy the expandable implant 22 within the vertebral body, visualize the expandable implant 22 on fluoroscopy, make any desired adjustments to the axial position or rotational orientation of the expandable implant 22, and then anchor the device 20 in the desired position.

The cam 84 includes a cam distal end 86 and a cam proximal end 88. The cam distal end 86 and the cam proximal end 88 may define a length of the cam 84, which may correspondence to a distance between a distal-most one of the anchoring elements 62 and proximal-most of the anchoring elements 62. The corresponding lengths provide for a single input (i.e., the second input) to simultaneously deploy the anchoring elements 62. Alternatively, the cam 84 may be dimensioned or contoured to provide for staged deployment of less than all of the anchoring elements 62. Starting with FIG. 9A, each of the expandable implant 22 and the pedicle anchor 24 are in the insertion configuration. The rod 66 is in a first axial position in which the cam distal end 86 is positioned distal to the distal-most one of the anchoring elements 62. The first input to the actuator 50 translates the rod 66 from the first axial position to a second axial position in which the tissue support ski 26 is moved away from the longitudinal axis in the manner previously described. The expandable implant 22 is in the deployed configuration, and the pedicle anchor 24 remains in the insertion configuration. The translation of the rod 66 to the second axial position, in addition to deploying the expandable implant 22, moved the cam 84 into axial alignment with the proximal-most one of the anchoring elements 62, as shown in FIG. 9B. Once positioning of the expandable implant 22 is confirmed, the second input rotates the rod 66 to rotate the cam 84 to deploy the anchoring elements 62 and move the pedicle anchor 24 to the anchored configuration. The present implementation may also include a locking mechanism to provide irreversibility to the deployment of the device 20.

Referring now to FIG. 10-13, another implementation of the device 20 is shown in which the outer profile of the device 20 may be elliptical or oval, as previously mentioned. Should an oval bore be established through the vertebral pedicle, the device 20 of the present disclosure may be introduced through the oval bore. Particularly with the anchor body 60 being oval-shaped, relative rotation between the anchor body 60 and the oval bore within the vertebral pedicle is prevented. This may lessen or obviate the need for the anchoring elements 62, as shown in FIG. 10; however, the anchoring elements 62 or modifications thereof may be included to prevent axial movement of the device 20 relative to the vertebra.

As mentioned, the expandable implant 22 being oval-shaped provides for the tissue contact surface 54 being larger. The tissue contact surface 54 is oriented along or parallel to the width that is greater than the height, as shown in FIG. 13. The arrangement results in the tissue support ski 26 being oriented laterally after the expandable implant 22 is inserted through the oval bore and into the vertebral body. However, as previously described, it is preferable for the tissue support ski 26 to be moved upwardly to urge the upper endplate of the vertebral body cranially to the desired restored height. As such, the present implementation provides means for rotating the expandable implant 22 relative to the pedicle anchor 24 that remains rotationally constrained within the oval bore. In one example, the expandable implant 22 may be rotated approximately 90 degrees relative to the pedicle anchor 24.

The expandable implant 22 may include proximal engagement features 90 configured to be operably coupled with distal engagement features 92 of the pedicle anchor 24. More particularly, a proximal surface of the proximal end element 30 may be formed with teeth, and a distal surface of the anchor body 60 may be formed with complementary teeth. The teeth may be unidirectional and eccentrically-shaped to provide a ratchet-like effect. In other words, the expandable implant 22 may be configured to permit rotation relative to the pedicle anchor 24 in a first rotational direction, and prevent rotation relative to the pedicle anchor 24 in a second rotational direction opposite the first rotational direction.

To facilitate rotating the expandable implant 22 relative to the pedicle anchor 24, the rod 66 of the actuator 50 may include a head portion 94. The head portion 94 is noncircular in cross-section. The expandable implant 22, and more particularly the proximal end element 30, defines a keyway 96 that is noncircular in cross-section in a manner generally complementary to the head portion 94 of the rod 66. For example, FIG. 10 shows the head portion 94 being rectangular and at least a portion of the keyway 96 being rectangular. The engagement of the noncircular components prevents relative rotation, and therefore the input to the actuator 50 to rotate the rod 66 in the first rotational direction correspondingly rotates the expandable implant 22. The expandable implant 22 may be introduced into the vertebral body in the orientation shown in FIG. 10, after which with the rotation of the expandable implant 22 relative to the pedicle anchor 24 assumes the orientation shown in FIG. 11. The oval shape of the anchor body 60 remains oriented upwardly and downwardly, whereas the tissue support ski 26 of the expandable implant 22 is now also oriented cranially as desired.

In the configuration show in FIG. 11, relative rotation of the expandable implant 22 relative to the pedicle anchor 24 in the second rotational direction is prevented by the engagement of the distal and proximal engagement features 90, 92. However, further rotation of the expandable implant 22 relative to the pedicle anchor 24 in the first rotational direction is not fully prevented. The desired magnitude of rotation necessary to orient the expandable implant 22 cranially is known in most cases based on the design of the device, the device 20 may include a blocking feature 98 configured to prevent further rotation of the expandable implant in the first rotational direction to greater than a predetermined angle. The predetermined angle may be approximately 90 degrees, or more generally within the range of 80 to 100 degrees. The blocking feature 98 may be protrusions defined a distal end of the bore 68 of the anchor body 60. The protrusions are radially oriented to interfere with the head portion 94 of the rod 66 when the rod 66 is at the predetermined angle. In a sense, the head portion 94 of the rod 66 is a complementary blocking feature. The blocking feature 98 permits bidirectional relative rotation of the expandable implant 22 relative to the pedicle anchor 24 within a predetermined range. However, the distal and proximal engagement features 90, 92 prevent relative rotation in the second rotation direction, and thus cooperate with the blocking feature 98 to effectively lock the expandable implant 22 in the desired rotational orientation. In other words, for example, once the expandable implant 22 is rotated relative to the pedicle anchor 24 in the first rotational direction by 90 degrees, further rotation in the first rotational direction is prevented by the blocking feature 98 and rotation of in the second rotational direction is prevented by the distal and proximal engagement features 90, 92.

Systems for augmenting the vertebra utilizing the device 20 are contemplated. In addition to the access cannula and introducer device, the system may include a posterior element configured to be coupled to the expandable implant, and optionally, a spinal rod configured to be coupled to the posterior element in a spinal fusion procedure. The posterior element and the spinal rod may be indicated for spinal fusion procedures in which the device 20 is deployed in adjacent vertebrae. In one example, the posterior element is secured to the anchor body 60. In certain implementations, the system may include instrumentation configured to create the oval bore. The system may include a first material removal device configured to create a pilot hole within the pedicle, a second material removal device configured to augment the pilot hole into an oval bore through the pedicle. The first material removal device may be a drill, reamer, or the like, and the second material removal device may be a bur, awl, or the like. While in many implementations the system may be cementless, it is understood that the system may include a bone cement delivery system configured to deliver bone cement through the pedicle anchor 24 and into the vertebral body to interdigitate with the expandable implant 22 and the cancellous bone.

Certain inventive methods may be described with reference to the following exemplary clauses:

Clause 1—A method of augmenting a vertebra with a device including an expandable implant, a pedicle anchor coupled to the expandable implant, and an actuator, the method including the step of providing an input to the actuator to move a rod within an anchor body of the pedicle anchor to move the expandable implant from an insertion configuration in which a tissue support ski is within an outer profile of the device to a deployed configuration in which (i) a distal end element is moved towards a proximal end element to cause a distal strut and a proximal strut to move the tissue support ski away from a longitudinal axis of the device, and (ii) at least one anchoring element is moved to extend beyond the anchor body relative to the anchor body and into engagement with a vertebral pedicle of the vertebra.

Clause 2—The method of clause 1, wherein the input a single input to simultaneously deploy the expandable implant and the pedicle anchor.

Clause 3—The method clause 1, wherein the input is a first input and a second input, the method including: providing the first input to the actuator to translate the rod within the anchor body to move the expandable implant from the insertion configuration to the deployed configuration, and to axially align a cam of the rod with the at least one anchoring element; and providing the second input to the actuator to rotate the rod within the anchor body to cause interference between the cam and the at least one anchoring element.

Clause 4—The method of clause 3, further including confirming a position of the expandable implant after the step of providing the first input and prior to the step of providing the second input.

Clause 5—A method of augmenting a vertebra with a device including an expandable implant, a pedicle anchor coupled to the expandable implant, and an actuator, wherein the expandable implant and the pedicle anchor are oval-shaped, the method including the steps of: directing the expandable implant through an oval bore within a vertebral pedicle and to within a vertebral body; providing a first input to an actuator to rotate the expandable implant relative to the pedicle anchor; and providing a second input to the actuator to move a rod within an anchor body of the pedicle anchor to deploy the expandable implant within the vertebral body.

Clause 6—The method of clause 5, wherein the step of providing the first input further includes rotating a head portion of the rod in a first rotational direction, wherein the head portion is rotationally constrained within the expandable implant.

Clause 7—The method of clause 6, wherein the step of providing the first input further includes rotating the head portion until a blocking feature of the expandable implant prevents further rotation of the rod in the first rotational direction.

Clause 8—The method of clause 7, further including ensuring relative rotation of the expandable implant relative to the pedicle anchor is prevented by attempting to rotate the rod in a second rotational direction opposite the first rotational direction, wherein complementary engagement features of the expandable implant and the pedicle anchor prevent rotation in the second rotational direction.

Clause 9—The method of any one of clauses 5-8, further including creating a pilot hole within the vertebral pedicle with a first material removal; and augmenting the pilot hole into the oval bore with a second material removal device.

Clause 10—The method of any one of clauses 1-9, further including coupling a posterior element to the pedicle anchor; and coupling a spinal rod to the posterior element.

The foregoing disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A device for augmenting a vertebra including a vertebral body and a vertebral pedicle, the device comprising:
    an expandable implant comprising a distal end element and a proximal end element defining a longitudinal axis, a tissue support ski, a distal strut coupled to the distal end element and the tissue support ski, and a proximal strut coupled to the proximal end element and the tissue support ski, wherein the expandable implant is configured to be deployed within the vertebral body by moving the distal end element towards the proximal end element to cause the distal strut and the proximal strut to move the tissue support ski away from the longitudinal axis;
    a pedicle anchor coupled to the expandable implant and comprising an anchor body, and at least one anchoring element movably coupled to the anchor body; and
    an actuator movable within the anchor body of the pedicle anchor and the expandable implant, wherein the actuator is configured to be actuated by a user to deploy the at least one anchoring element into engagement with the vertebral pedicle.

2. The device of claim 1, wherein the actuator is secured to the distal end element and the anchor body is coupled to the proximal end element, wherein the actuator is configured to draw the distal end element towards the proximal end element against resistance from the proximal end element by the pedicle anchor.

3. The device of claim 1, wherein the anchor body defines a bore, and wherein the actuator is a rod extending through the bore.

4. The device of claim 1, wherein each of the tissue support ski and the at least one anchoring element are configured to be moved in a same plane of expansion.

5. The device of claim 1, wherein deployment of the expandable implant is configured to be simultaneous with deployment of the pedicle anchor.

6. The device of claim 1, wherein the at least one anchoring element comprises spikes or fingers extending from material webs integrally formed with the anchor body.

7. The device of claim 1, further comprising a strut hub coupled to the tissue support ski, wherein the distal strut extends between the distal end element and the strut hub and the proximal strut extends between the proximal end element and the strut hub.

8. The device of claim 7, further comprising:
    a second distal strut secured to the distal end element and the strut hub; and
    a second proximal strut secured to the proximal end element and strut hub.

9. The device of claim 7, wherein the distal strut is secured to the distal end element at an angle so as to be angled towards the tissue support ski in an undeployed configuration, and wherein the proximal strut is secured to the proximal end element at an angle so as to be angled towards the tissue support ski in the undeployed configuration.

10. The device of claim 1, further comprising a lower strut secured to the distal end element and the proximal end element.

11. The device of claim 1, further comprising:
    a distal truss secured to the distal end element and an upper surface of the distal strut; and
    a proximal truss secured to the proximal end element and an upper surface of the proximal strut.

12. The device of claim 1, wherein each of the distal end element and the proximal end element is oval so as to define an outer profile of the expandable implant that is an oval prism, wherein each of the expandable implant and the pedicle anchor comprise engagement features, and wherein the actuator is further configured to rotate the expandable implant relative to the pedicle anchor in a first direction and the engagement features are configured to prevent rotation of the expandable implant relative to the pedicle anchor in a second direction opposite the first direction.

13. The device of claim 12, wherein the tissue support ski comprises a tissue contact surface that is at least substantially planar and recessed from the outer profile of the expandable implant.

14. A device for augmenting a vertebra including a vertebral body and a vertebral pedicle, the device comprising:
    an expandable implant comprising a distal end element and a proximal end element defining a longitudinal axis, a tissue support ski, a distal strut coupled to the distal end element and the tissue support ski, and a proximal strut coupled to the proximal end element and the tissue support ski;
    a pedicle anchor comprising an anchor body defining a bore, and at least one anchoring element movably coupled to the anchor body; and
    an actuator comprising a rod extending through the bore and secured to the distal end element of the expandable implant, wherein the actuator is configured to be actuated by a user to move the at least one anchoring element relative to the anchor body and into engagement with the vertebral pedicle, and further deploy the expandable implant within the vertebral body by moving the distal end element towards the proximal end element to cause the distal strut and the proximal strut to move the tissue support ski away from the longitudinal axis.

15. The device of claim 14, wherein the rod comprises a knuckle configured to be moved into engagement with an inner surface of the at least one anchoring element with proximal translation of the rod relative to the anchor body.

16. The device of claim 15, wherein the knuckle comprises a barb configured to be moved into irreversible interference engagement with a complementary feature of the at least one anchoring element.

17. A device for augmenting a vertebra including a vertebral body and a vertebral pedicle, the device comprising:

an expandable implant comprising a distal end element and a proximal end element defining a longitudinal axis, a tissue support ski, a distal strut coupled to the distal end element and the tissue support ski, and a proximal strut coupled to the proximal end element and the tissue support ski, wherein the expandable implant is configured to be deployed within the vertebral body by moving the distal end element towards the proximal end element to cause the distal strut and the proximal strut to move the tissue support ski away from the longitudinal axis;

a pedicle anchor coupled to the expandable implant and comprising an anchor body, and at least one anchoring element movably coupled to the anchor body, wherein the pedicle anchor is configured to be deployed into engagement with the vertebral pedicle; and an actuator coupled to the expandable implant and the pedicle anchor, wherein the actuator is configured to be actuated by a user to one of (i) deploy the expandable implant without deployment of the pedicle anchor, and (ii) deploy the pedicle anchor without deployment of the expandable implant, wherein the actuator is a rod comprising a cam configured to be rotated into engagement with an inner surface of the at least one anchoring element with rotation of the rod relative to the anchor body.

18. The device of claim 17, wherein the rod is configured to be translated within the anchor body to an axial position in which the cam is in alignment with the at least one anchoring element.

19. The device of claim 18, wherein translation of the rod is configured to deploy the expandable implant.

\* \* \* \* \*